(12) United States Patent
Butson

(10) Patent No.: US 10,688,316 B2
(45) Date of Patent: Jun. 23, 2020

(54) MEDICAL SHIELD

(71) Applicant: Butsonian Enterprises Pty Ltd, Epping (AU)

(72) Inventor: Macinley Butson, Wollongong (AU)

( * ) Notice: Subject to any disclaimer, the term of this patent is extended or adjusted under 35 U.S.C. 154(b) by 0 days.

(21) Appl. No.: 16/004,482

(22) Filed: Jun. 11, 2018

(65) Prior Publication Data

US 2019/0374793 A1    Dec. 12, 2019

(51) Int. Cl.
*A61N 5/10* (2006.01)
*G21F 1/00* (2006.01)
*G21F 3/00* (2006.01)

(52) U.S. Cl.
CPC ............... *A61N 5/10* (2013.01); *G21F 1/00* (2013.01); *A61N 2005/1094* (2013.01); *G21F 3/00* (2013.01)

(58) Field of Classification Search
CPC .... A61N 5/10; A61N 2005/1094; G21F 1/00; G21F 3/00

USPC .......... 250/515.1, 516.1, 517.1, 518.1, 519.1
See application file for complete search history.

(56) References Cited

U.S. PATENT DOCUMENTS

| | | | |
|---|---|---|---|
| 2006/0183959 A1* | 8/2006 | Sioshansi | A61N 5/1084 600/3 |
| 2015/0004131 A1* | 1/2015 | Milstein | G21F 3/025 424/85.2 |
| 2016/0324490 A1* | 11/2016 | Brachman | A61B 6/107 |

* cited by examiner

*Primary Examiner* — Nicole M Ippolito
(74) *Attorney, Agent, or Firm* — Darren Gardner

(57) ABSTRACT

To provide patient shielding of non-treatment areas bordering a treatment zone of the patient during radiation therapy, a shield device may be located on the patient. The shield device has a plurality of interconnected and overlapping elements, e.g. in a scale maille arrangement, that forms a conformal sheet that can be laid over the shielded portion of the patient, e.g. over the contralateral breast during breast cancer treatment. The edge of the scale maille sheet is substantially configurable and can be made to conform to the field edge of the treatment zone on the patient.

16 Claims, 10 Drawing Sheets

MEDICAL SHIELD

FIELD OF THE INVENTION

This disclosure relates to devices that can be used by patients during medical procedures and in particular radiation procedures. The device has particular application as a shield in breast cancer radiotherapy though it is not intended to be limited to this treatment only.

BACKGROUND OF THE INVENTION

One in eight women will develop breast cancer in their lifetime and it is the most common cancer in women. It is recommended that radiotherapy treatment is delivered after initial surgery for breast cancer to substantially reduce the risk of site specific relapse. However, during breast cancer treatment using radiotherapy, the other breast (the contralateral breast) receives radiation dose as an unwanted side effect of the treatment. The association between low dose from peripheral ionizing radiation and the risk for secondary cancer has attracted interest specifically for the long-term surviving patients. Specifically, concerns regarding oncogenesis and second cancer induction are realized and invoke the need for ALARA (As Low As Reasonably Achievable) principles to be followed.

During radiation therapy, regardless of the treatment technique, the surrounding normal tissue outside the treated area inevitably receives some amount of radiation dose. Such dose outside the geometric boundaries of the treatment fields is known as peripheral dose. There are three main sources of peripheral dose: (a) leakage through the treatment collimation (x-rays); (b) scattered radiation from the secondary collimators and beam modifiers such as the Multi-Leaf Collimator (MLC), physical wedges (x-rays and electrons); and (c) internal scatter originating in the patient (x-rays). It has been shown that peripheral doses can be as large as 20% of maximum dose for normally incident beams and that these values can increase with oblique angle of incidence.

To minimize radiation doses delivered to the contralateral breast, lung, and heart, some patients can be treated with a prone technique. If a supine treatment is used, to reduce contralateral breast dose, different types of shielding devices, and delivery techniques have been used. These include mobile high-density lead shields placed between the treatment machine and the patient. Other devices used were tissue-density superflab material laid over the patient's contralateral breast. Although these methods did reduce contralateral breast dose, they presented technical difficulties in their usage. Mobile lead shields need to be placed appropriately between the patient and the treatment head of the linear accelerator (linac). Such techniques are not very efficient since they demand precise positioning alignments. They also suffer from not being able to be shaped around the treatment field edges. Superflab bolus can also reduce skin and subcutaneous dose but it requires at least 10 mm thickness of bolus material to provide sufficient attenuation. This process may also introduce misalignment errors near the edge of the treatment fields.

What is required is an improved shielding method and device.

SUMMARY OF THE INVENTION

To provide patient shielding of non-treatment areas bordering a treatment zone of the patient during radiation therapy, a shield device may be located on the patient. The shield device has a plurality of interconnected and overlapping elements, e.g. in a scale maille arrangement, that forms a conformal sheet that can be laid over the shielded portion of the patient, e.g. over the contralateral breast during breast cancer treatment. The edge of the scale maille sheet is substantially configurable and can be made to conform to the field edge of the treatment zone on the patient.

In one aspect of the disclosure, there is provided a method for providing shielding to a patient during a radiation treatment. The method may include locating at least one shield device over at least one portion of the patient to be shielded. The at least one shield device may include a plurality of overlapping and interconnected shield elements that form a sheet including at least one substantially configurable edge. The method may include substantially aligning at least one configurable edge of the at least one shield device with at least one field edge of a treatment zone of the patient to leave the treatment zone exposed, and subjecting the patient to a radiation treatment.

In one aspect of the disclosure, there is provided a device for use in radiation therapy of a patient, the device including a plurality of overlapping and interconnected shield elements that form a sheet including at least one configurable edge, wherein the at least one configurable edge is able to be configured to substantially conform to a field edge of a radiation treatment zone of a patient during a radiotherapy procedure.

BRIEF DESCRIPTION OF THE DRAWINGS

Reference will now be made, by way of example only, to specific embodiments and to the accompanying drawings in which.

DETAILED DESCRIPTION OF THE INVENTION

Figure 1:
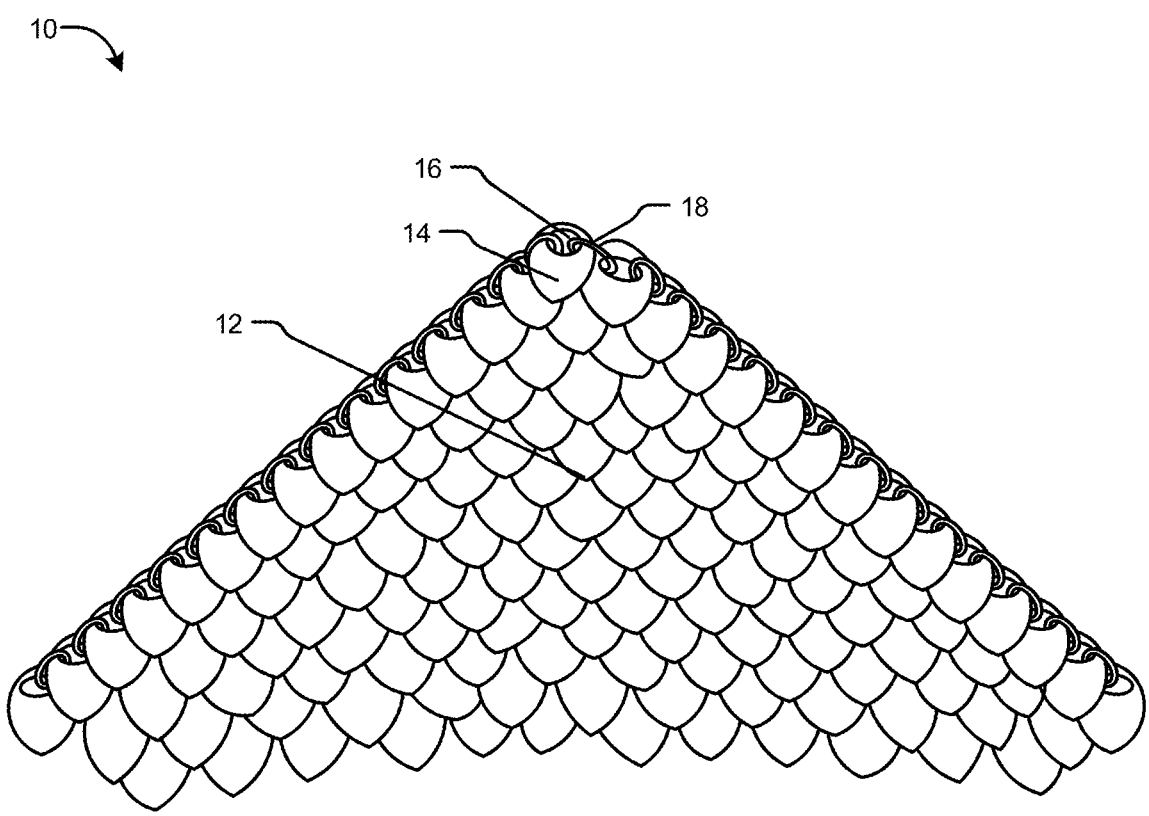
FIG. 1 depicts a portion of a sheet of a shield device.

In FIG. 1, there is shown a portion of a device or shield 10 during manufacture and assembly. The device 10 includes a sheet 12 including a plurality of individual shield elements 14, such as plates or scales, that are interconnected and arranged in overlapping patterns to form the sheet. The individual plates may each include one or more holes 16 that allow attachment means to join adjacent elements to each other. In one embodiment, the attachment means may be rings 18, e.g. metal rings, though other attachment means may be contemplated including non-metal rings, threads, rivets, etc.

In general, the sheet may be referred to as a scale maille sheet and many methods for forming scale maille are known. While scale maille refers to specific arrangements of the plates, other interlocking plate or scale arrangements may be contemplated. For example, other plate arrangements may be generally referred to as lamellar armor.

At times throughout the present specification and in the Figures, the device 10 may be referred to using the Applicant's proprietary term Smart Armour.

Figure 2A:
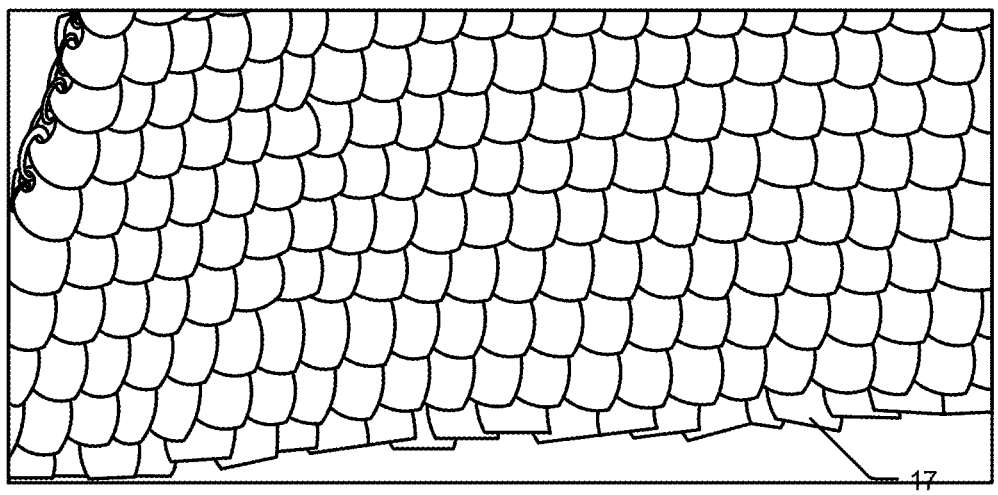
FIG. 2A depicts a front surface of a shield device.
Figure 2B:
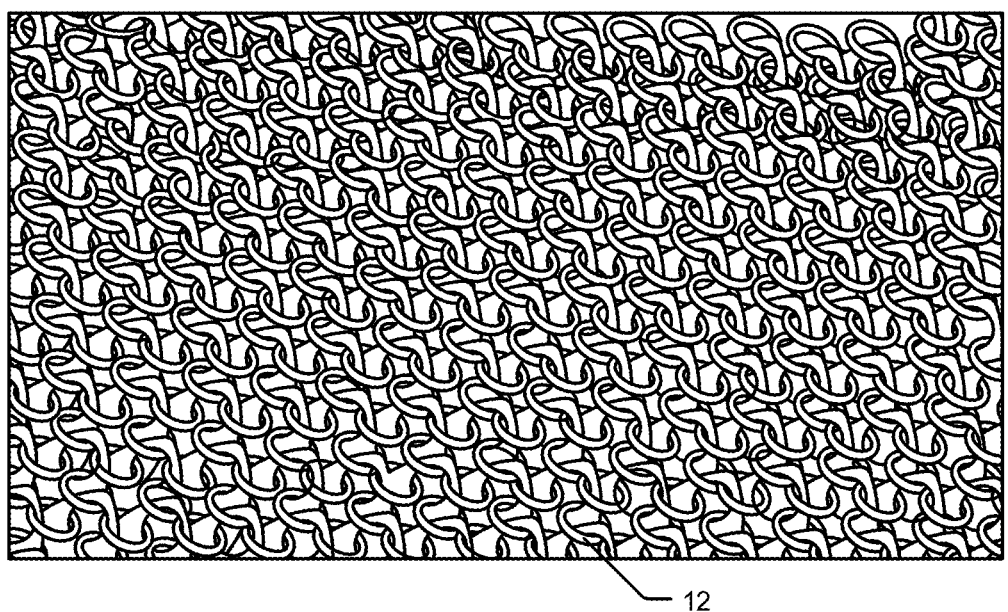
FIG. 2B depicts a back surface of a shield device.

FIG. 2 shows a more fully assembled form of the sheet of FIG. 1 that can be used to reduce contralateral breast dose during radiation. In one particular embodiment, the device 10 is made from 12 mm×22 mm×0.6 mm thick copper scales, interwoven together to form a scale maille design as shown in FIGS. 2a and 2b. Conventional scale maille weaving techniques may be employed to create the scale maille. This utilizes the use of 7 mm diameter jumper rings linked together and the 0.6 mm thick copper scales threaded over the jumper rings through a 2 mm diameter hole located at the top of each copper scale. By interweaving the scale maille pattern, the 0.6 mm thick copper scales overlap producing a 1.2 mm thick copper shield at all points. The underside of the scale maille is shown in FIG. 2b. As is shown in FIG. 2b, the jumper rings may be of copper, though other metals or non-metals may similarly be used.

In the embodiment of FIG. 1, a typical scale, i.e. within the body of the sheet, is linked to four adjacent scales, being the four scales diagonally above and below the respective scale, in the orientation depicted in FIG. 1. The upper portion of the scale underlies the scales above, while the lower portion overlies the scales below. Other overlapping and interconnecting configurations are possible and are considered within the scope of the present disclosure.

In one embodiment, the device 10 has dimensions of 30 cm×30 cm×0.3 cm thick. This is considered sufficient to cover a typical contralateral breast. In other embodiments, the device 10 may be of any suitable size for use in shielding any required part of the body during other radiation therapy treatments.

The shield elements 14 are not rigidly locked to each other but rather, the means by which the shield elements 14 are interconnected allows for a degree of movement between adjacent elements. Within the body of the sheet, this degree of movement allows the sheet to conform to various shapes, in particular various shapes of the body. At the edge of the sheet, the shield elements are sufficiently displaceable to allow the shape of the edge to be configured to various shapes, including straight edges, angles, and curves. As will be made apparent below, this degree of configurability has particular advantages for allowing the shield to be used at a non-straight edge of a radiation treatment zone of a patient, while allowing the treatment zone to remain exposed.

Figure 3:
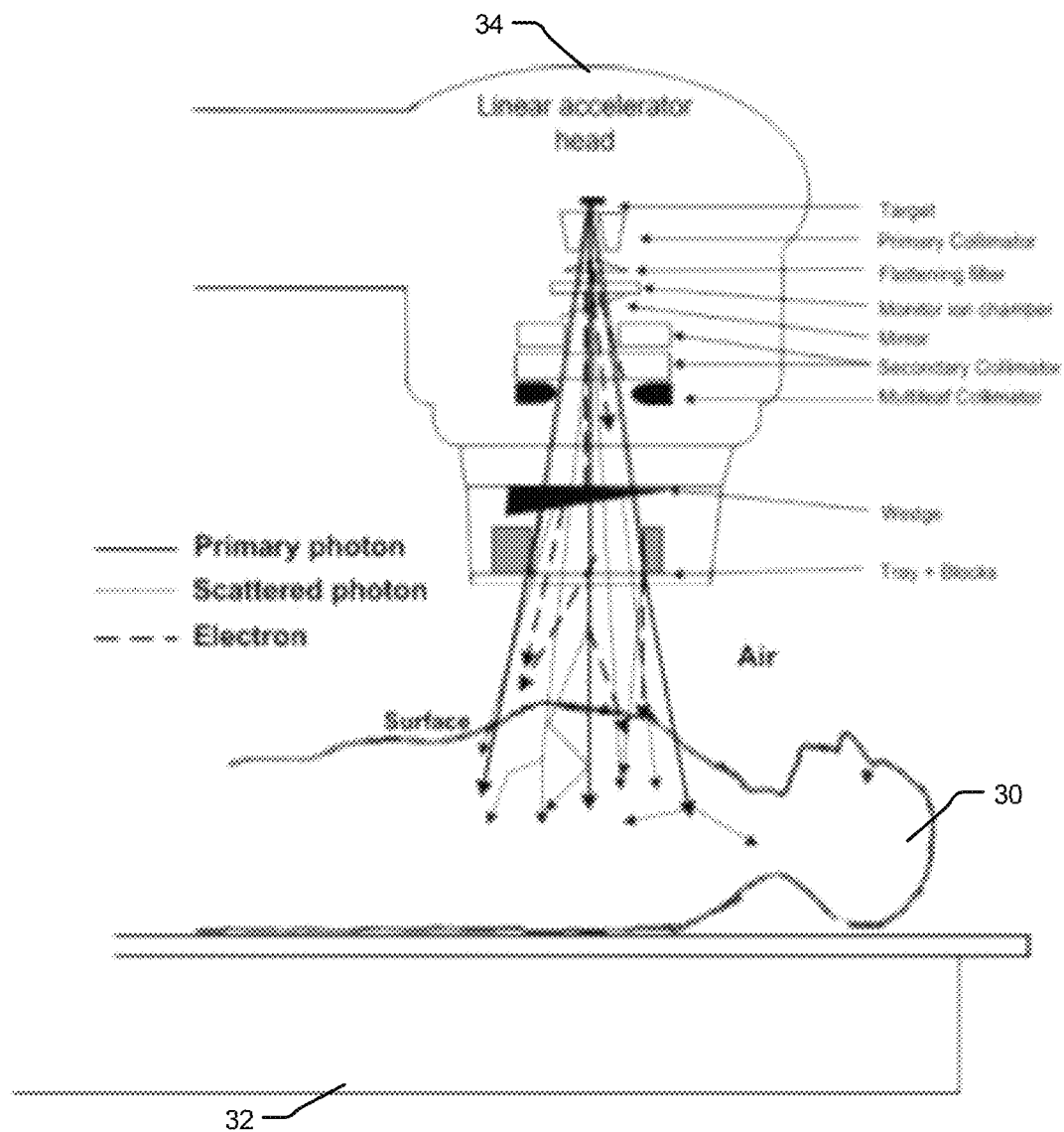
FIG. 3 depicts an arrangement for radiation therapy on a patient.

A typical radiation therapy device is depicted in FIG. 3. FIG. 3 shows a patient 30 lying supine on a treatment table 32. A linear accelerator head (linac) 34 is disposed above the patient. For most breast radiation treatments, the linear accelerator 34 will be located to one side of the patient to provide a tangential radiation dose.

As can be seen from FIG. 3. the patient may be subject to radiation from primary photos, secondary photons and electrons. Portions of the patient outside of a treatment zone may receive some of this radiation, known as a peripheral dose. In breast cancer treatment, for example, the linac 34 tends to be located on the contralateral breast (untreated breast) side of the patient so that the radiation is incident at an angle to the patient, known as tangential treatment. The contralateral breast can therefore be subject to a significant peripheral dose of radiation.

During radiation therapy for breast cancer treatment and the like, the shield device 10 can be draped over the contralateral breast region, ensuring that the shield does not interfere with any entry fields. This would cause increases in skin dose due to build up dose effects. The shield conforms to the breast shape and provides protection during treatment. The shield does not need to be present during simulation or CT as it does not affect treatment dose and treatment should not occur through the device.

The design of the shield allows the copper scales to overlap thus providing an approximate 1.2 mm thickness of copper over the entire region of the shield. The design allows the shield 10 to conform to the shape of the contralateral breast providing substantial coverage and shielding. The shield 10 has a configurable edge formed by multiple plates 14 and thus can be shaped to follow the irregular field edges required by typical cancer treatments for radiotherapy. The shield 10 can be handled safely as it is made from copper, and is thus nontoxic and can be easy for radiation therapy workers to use on patients.

Shielding properties of various metals have been studied in the peripheral region of 6 MV x-ray beams produced by a Varian 6EX linear accelerator (Varian Medical Systems, Palo Alto, Calif., USA). The materials evaluated were 1.0 mm thick aluminum, 1.0 mm copper, and 1.0 mm lead sheets. Dose measurements were performed in RMI solid water (RMI, Middleton, Wis., USA) using an Attix model 449 parallel plate ionization chamber (RMI, Middleton Wis., USA) at depths of 1 mm, 2 mm, 3 mm, 5 mm, 10 mm, and 15 mm. Measurements were made 5 cm away from the edge of the primary field which was a 10 cm×20 cm field size at 100 cm source to surface distance (SSD). Results were compared to measured percentage dose at the same peripheral position for an open field with no metal shielding in place. The results were normalized to 100% at the depth of maximum dose at the central axis of the primary radiation field (depth of 15 mm). The measurements were repeated 6 times for uncertainty analysis. Errors were calculated as 2 standard deviations of the mean for all measurements taken at each measurement point. These errors combine both type A and type B errors associated with uncertainty in set up as well as deviations in measurement accuracy. Errors are expressed as the square root of the sum of the squares of each error in relation to measurements made and is expressed by:

$$\delta R = \sqrt{[(\delta x)^2 + (\delta y)^2 + (\delta x)^2]}$$

where δR is the total error, and δx, δy, and δz represent each component of measured uncertainty.

Dose measurements were also made on the shielding characteristics of a scale maille designed peripheral dose shield.

Figure 4:
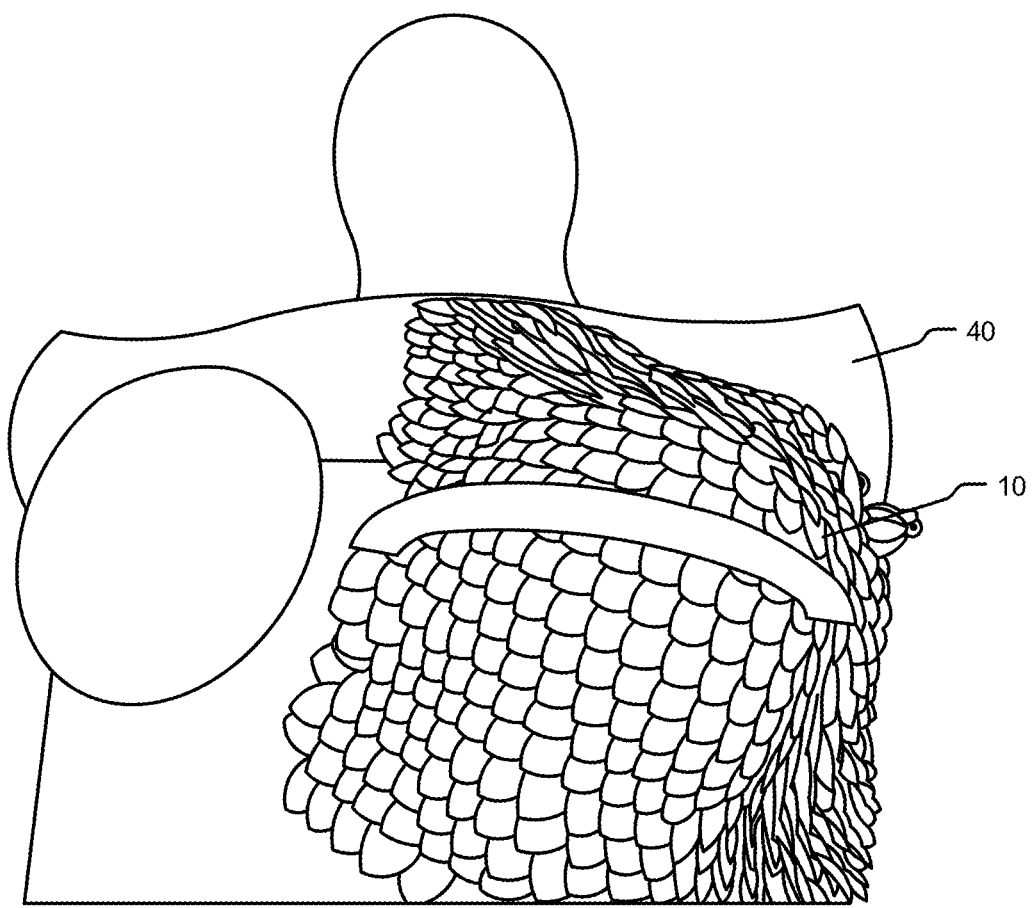
FIG. 4 depicts a shield device depicted on a dummy patient.

To evaluate contralateral breast shielding, an ART anthropomorphic phantom 40, as shown in FIG. 4, was positioned on a Varian 21EX linear accelerator and treated with a conventional 10 cm×20 cm asymmetric parallel opposed field size using a medial and tangent beam configuration with 6 MV x-ray beams. Skin doses were measured using a Gafchromic EBT3 film (Ashland Inc, New Jersey, USA) from 5 cm inside the medial edge of the medial beam and across the contralateral breast (covered by shield 10 in FIG. 5). Gafchromic films have been shown to be suitable for accurate skin dosimetry. Again, the measurements were repeated six times for reproducibility and uncertainty analysis. The doses were normalized to 100% delivered dose at the midpoint position in the treated breast. The skin dose results were compared to percentage dose results delivered without the shield 10 in position. The measured dose represented the sum of radiation dose delivered from both the medial and lateral beams. To evaluate the shield using different types of clinical treatments, five clinical plans from different patient treatments were delivered to the ART phantom and skin dose assessed with and without the shield.

The five patient treatments delivered included, patient one, using enhanced dynamic wedge fields, patients two and three, using field in field techniques, and patients four and five, using a hybrid intensity modulated radiation therapy (IMRT) technique. Physical wedges were not used for patient treatments and thus were not evaluated. Results for skin dose were measured using the same techniques as the open field measurements. To perform the irradiations, the patient plans were transferred to the ART phantom CT dataset for planning and treatment delivery. It is acknowledged that the plans would not be optimized due to differences in anatomy; however, this work would highlight differences in contralateral breast skin dose delivered, with and without the shields.

Figure 5:
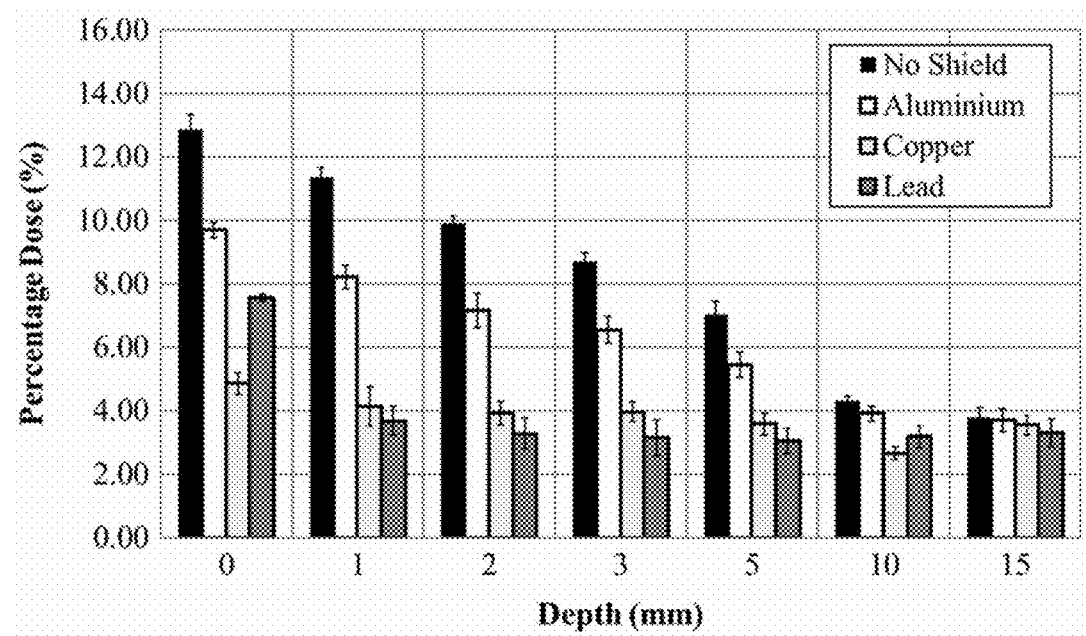
FIG. 5 depicts a comparison of the shielding properties of different materials.

FIG. 5 shows the results measured for attenuation of the radiation beam when the different metals are used to attenuate radiation in the beams peripheral region and compared to no shield results. Results were measured at depths ranging from 0 mm (at the skin surface) down to 15 mm, well beyond the subcutaneous tissue region. As can be seen in this configuration, at the surface when no shield was in place, approximately 13% of maximum dose was delivered. This was reduced to 9.5% for aluminum, 4.5% for copper and 7.2% for lead. A comparison of these values in dose reductions for three metals is shown in Table 1. For example, at 5 mm depth, the aluminum provides a 22.5% reduction in dose, whereas the copper and lead achieve 49% and 56.7% reductions, respectively.

TABLE 1

Peripheral skin dose reduction with metal shields.
Dose reduction achievable with various metals.

| Depth (mm) | Aluminum | Copper | Lead |
|---|---|---|---|
| 0 | 24.6 ± 4.2 | 62.2 ± 4.6 | 41.2 ± 3.8 |
| 1 | 27.6 ± 3.7 | 63.6 ± 5.3 | 67.6 ± 4.3 |
| 2 | 27.5 ± 4.7 | 60.3 ± 3.5 | 66.8 ± 4.4 |
| 3 | 24.6 ± 3.9 | 54.3 ± 3.3 | 63.9 ± 5.0 |
| 5 | 22.5 ± 4.5 | 49.0 ± 4.2 | 56.7 ± 4.4 |
| 10 | 9.4 ± 2.2 | 38.1 ± 2.1 | 26.3 ± 3.0 |
| 15 | 2.6 ± 3.6 | 6.6 ± 3.3 | 13.2 ± 4.2 |

Figure 6:
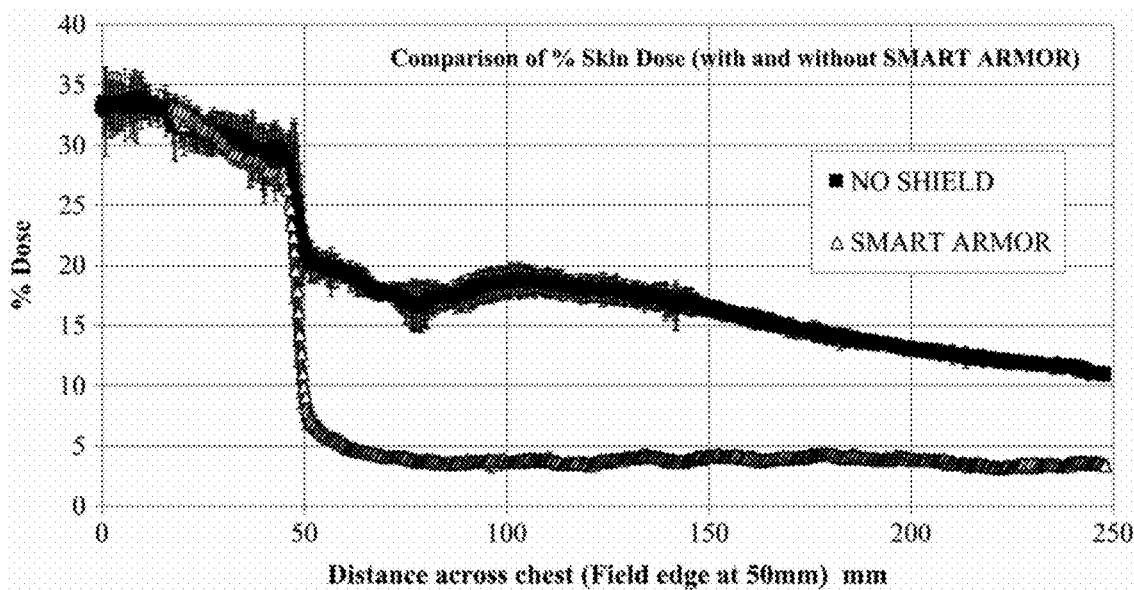
FIG. 6 depicts a comparison of radiation skin dose with and without a shield device.

FIG. 6 shows a dose profile measured across the chest wall of the anthropomorphic phantom, with and without the shield in place. The results are measured at an equivalent depth of 0.125 mm which is the effective point of measurement of EBT3 film. The results are normalized to 100% at the midpoint in the treated breast. In this example, the skin dose within the treatment field is similar with and without the shield being approximately 30-35% of maximum. However, in the peripheral region (from 50 mm distance onwards), the skin dose has been substantially reduced by the presence of the SMART Armor being reduced from as high as 16% down to approximately 4%. This represents an up to 75% reduction in dose achievable in the contralateral breast region with the use of the SMART Armor.

Figure 7:
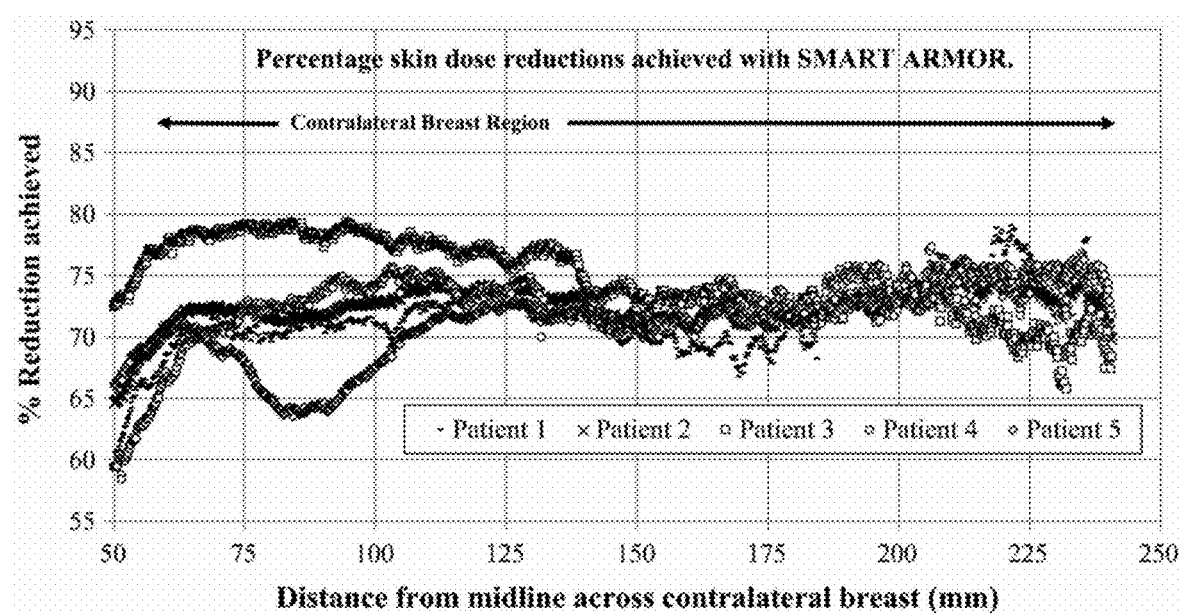
FIG. 7 depicts a percentage skin dose reduction using a shield device.

FIG. 7 shows the results for percentage dose reductions achievable across the chest wall of the anthropomorphic phantom. As can be seen, variations in contralateral breast dose with and without the SMART Armor range from approximately 60% to 80% in all five cases studied. In all cases, substantial reductions in skin dose are measured whether the treatment technique utilized enhanced dynamic wedges, field in field techniques, or hybrid IMRT dose delivery.

Dose delivered to the peripheral skin and subcutaneous regions during clinical radiotherapy is mainly caused by incident electron contamination from the entry beams. This contamination originates from production in the air column and the linear accelerator head. As such, substantial attenuation of this dose can be achieved by peripheral shielding using high-density materials. Results as discussed herein highlight the dose reduction achievable. Of interest is the significant reductions achieved with 1.0 mm of copper which reduced dose levels to below 5% at all depths. This value decreased to just below 4% by 15 mm depth and the majority of the dose remaining at all depths is expected to be from internal radiation scatter and high-energy x-ray penetration which was capable of transmission through the linear accelerator tungsten jaws. As the reductions in dose were achieved by removal of electron contamination, dose from posterior beams will not negligibly reduce for the contralateral breast. As such, 1.0 mm of copper material could be considered a useful shielding thickness if dose to peripheral regions were required to be reduced. This is the case for the contralateral breast during breast cancer treatment. Interestingly, lead showed a unique and reproducibly higher dose level directly under its surface compared to copper producing an average 7.6% dose compared to 4.8%. At every other depth beyond the surface, the peripheral measured dose was less for lead than for copper. Our assumptions are that the lead is producing a small quantity of low energy radiation on the exit side which deposits a larger degree of dose at the phantom surface. This does not occur for copper. Aluminum has a much lower density than copper or lead, and thus provides less radiation shielding properties at all depths. As the skin is a radiation sensitive organ, these findings make copper a better suited radiation shield than lead for peripheral regions when 6 MV x-rays are used for radiotherapy treatment.

As copper is a strong but malleable material it also lends itself well to be used to construct flexible and maneuverable shielding using a scale maille design. The scale maille device can conform to the shape of the contralateral breast phantom with a configurable edge that can conform to the irregular shaped treatment field edge as well as providing substantial reductions in delivered peripheral dose. As copper is a nontoxic material and lasts a long time without perishing and/or oxidation, it is well suited for clinical use when a shield is required for reducing the contralateral breast dose. Reductions of up to 80% from original values were achieved with the shield for standard open field tangential treatments. When standard clinical treatments were evaluated including enhanced dynamic wedges, field in field and hybrid IMRT techniques, the dose reductions achieved using the shield remained high. In the five cases studied, the values for percentage dose reduction ranged from 60% up to 80% across the contralateral breast region. As such, the shield as herein described can provide substantial contralateral breast shielding during common supine breast irradiation techniques. The shield when used is only draped over the contralateral breast region and is not placed within the primary breast treatment field. No distinguishable change in primary breast dose was measured or expected with the use of the shield.

The shield 10, due to its weaved design, is easy to use clinically and takes approximately 30 seconds to align on the anthropomorphic phantom. Clinically this may take longer; however, any small increase in time for set up is warranted due to the substantial reductions in contralateral breast dose achieved.

High-density materials, such as copper, can provide substantial shielding effects in radiotherapy cancer treatment in the peripheral regions of megavoltage x-ray beams. Copper has been shown to be superior to lead as a choice of shielding material due to its ability to reduce skin dose to a lower level. Copper was also found to be a useful choice of material to create a scale maille style shield which can be used to provide protection to skin and subcutaneous tissue in peripheral regions during radiotherapy treatment. This is especially useful in treatment of breast cancer where dose to the contralateral breast can be reduced by up to 80% of original values.

While copper has been shown to provide enhanced results over some other materials such as lead, there may be applications for these and other materials in various embodiments. For example, many high density metals and alloys may be suitable, including, without limitation brass, stainless steel, lead, tin, tungsten, silver and gold.

FIGS. 1, 2a and 2b show a shield formed in a diamond pattern. The diamond pattern shield is shown in situ on the anthropomorphic phantom 40 in FIG. 4. In a diamond pattern, the scales are arranged in rows 13 (FIG. 1) that are at an angle, in particular a 45 degree angle, to the edge 15 of the device 10. A diamond pattern is considered the simplest form of scale maille pattern to manufacture.

In the embodiment shown, each scale or plate is generally leaf or tear-drop shaped having a longitudinal axis that extends perpendicular to the row. The plate is generally convex on the outer side (exposed side) of the shield with the main curve extending across the longitudinal axis, i.e. perpendicular thereto.

The particular scale shape of scale is shown for illustrative purposes only and is not intended to be limiting. Other scale designs may be utilized with equal effect.

Figure 8:
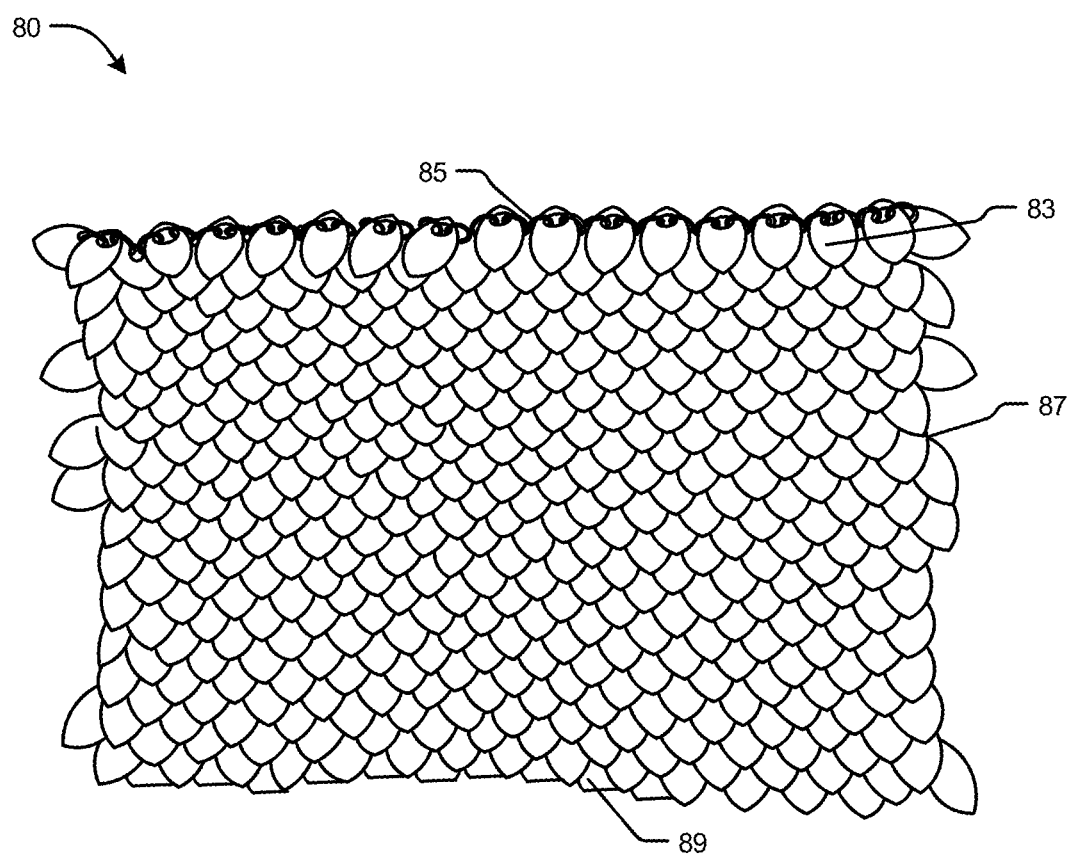
FIG. 8 depicts a front surface of an alternative embodiment of a shield device.
Figure 9:
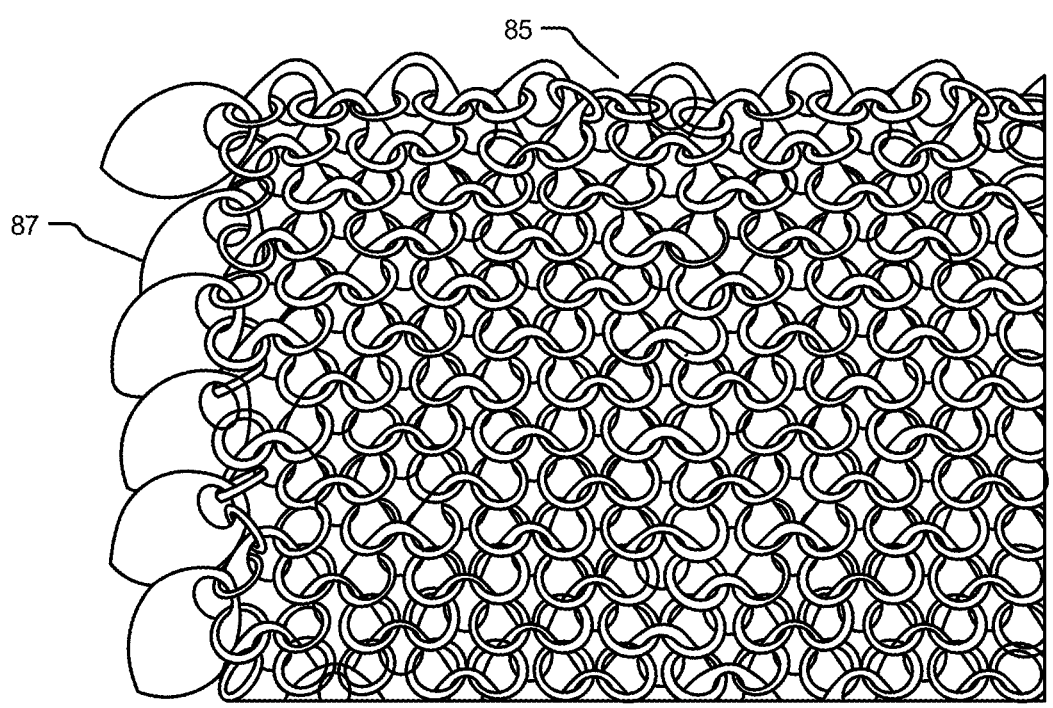
FIG. 9 depicts a back surface of the shield device of FIG. 8.

An alternative embodiment of a shield is depicted in front view in FIG. 8 and rear view in FIG. 9. In this embodiment, the shield 80 is formed in a rectangular pattern in which the rows 83 are generally parallel and perpendicular to the edges 85, 87 of the shield.

Figure 10:
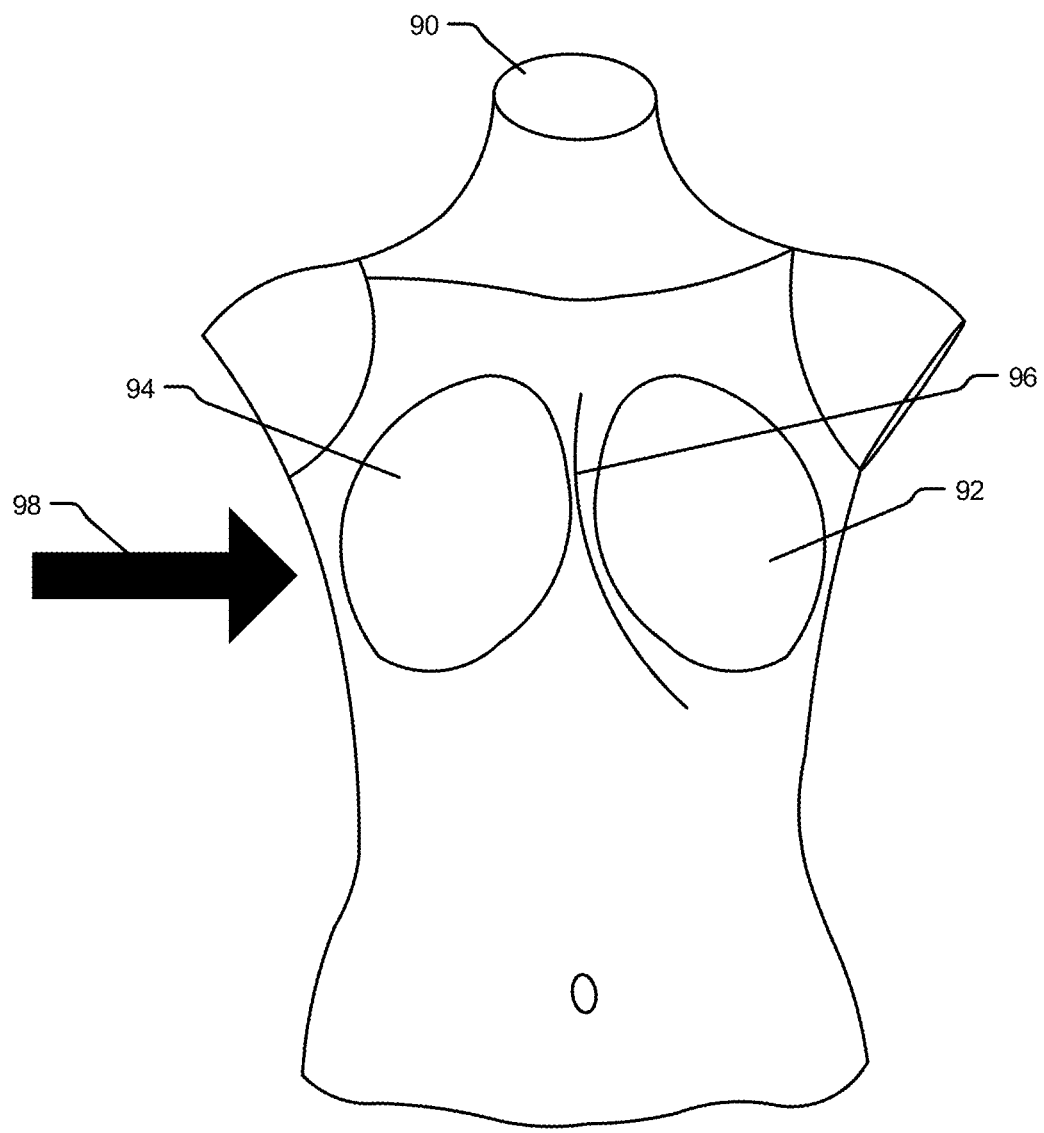
FIG. 10 depicts a dummy patient showing the border of a treatment zone.
Figure 11:
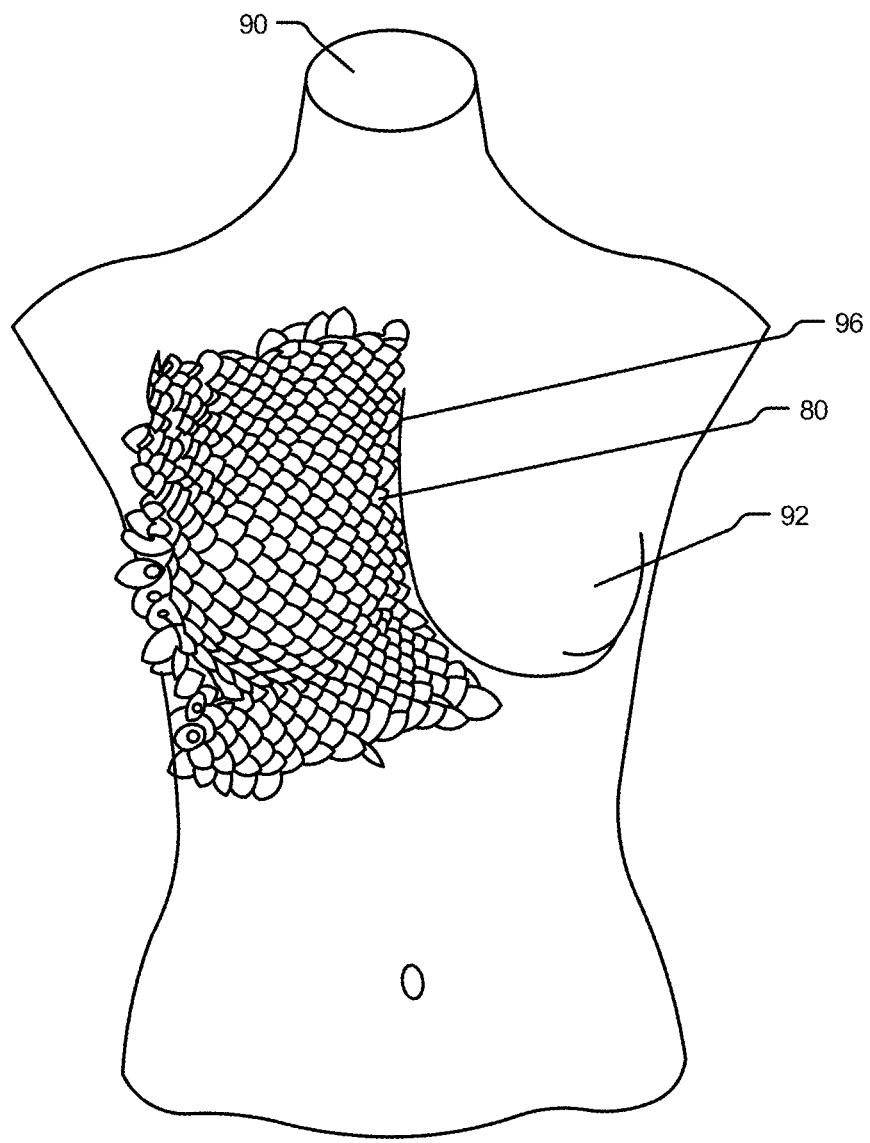
FIG. 11 depicts the dummy patient of FIG. 10 with a shield device located thereon.

FIG. 10 shows a dummy 90 simulating a patient that is to receive radiation treatment. The patient 90 includes the breast to be treated 92 and the contralateral breast 94. A field edge 96 that marks a boundary of the treatment region of the patient is shown. As depicted in FIG. 10, for tangential treatment, the linac would typically be located to the left of the patient in the orientation of FIG. 10. The patient would thus receive radiation incident in the general direction depicted by arrow 98. An issue with the diamond pattern as herein described is that, as shown in FIG. 4, it can be difficult to conform the edge of the shield 10 to the field edge 96. In addition, because the field edge is generally sagittal, the scale rows are generally located at an angle to the incident radiation, which may not provide the optimum shielding. When the rectangular pattern shield 80 of FIGS. 8 and 9 is placed over the contralateral breast 94 (FIG. 11), and the edge of shield is conformed to the substantially sagittal field edge 96, the rows of scales run generally perpendicular to the incident radiation with the plates more directly facing the incident radiation. Thus the radiation is less likely to penetrate any gaps between the scales.

As shown in FIG. 8, the scales along the lower edge 89 may be trimmed to form a straighter edge. This edge 89 may be used as the edge that is aligned and conformed to the field edge of the treatment region of the patient. Though, while each scale may have a generally straight edge, on the whole, the scales are sufficiently displaceable that the edge 89 remains sufficient configurable to form non-straight shapes that can tailor to match the typical edge of the treatment region.

While specific embodiments relating to the radiotherapy treatment of breast cancer has been described herein, it will be apparent to the person skilled in the art that the shield devices and methods for their use may extend to many other forms of shielding in patient treatments. The advantages of the shield device as herein described include that the shield has a conformal arrangement that can contour to many parts of the human body with a substantially configurable edge that can be conformed to a field edge of a treatment region, thereby allowing the peripheral dose received into non-treatment areas to be minimized. Further, while the treatment methods described herein show a single shield device being utilized at one edge of a treatment zone, the person skilled in the art will recognize that multiple shields may be deployed around multiple field treatment zone edges. In this way, the shields may be used to at least partially define the treatment zone that will be left exposed and thus subject to a dose of radiation during radiotherapy.

It will be understood by the person skilled in the art that terms of orientation such as top, bottom, front, back, left, right, inner, outer, etc. are used herein with reference to the drawings in order to provide a clear and concise description. Such terms are not intended to limit the examples and embodiments in any manner and the scope of the disclosure as defined herein will encompass other possible orientations of the components as will be perceived by the person skilled in the art.

Although embodiments of the present invention have been illustrated in the accompanied drawings and described in the foregoing description, it will be understood that the invention is not limited to the embodiments disclosed, but is capable of numerous rearrangements, modifications, and substitutions without departing from the spirit of the invention as set forth and defined by any claims that follow.

What is claimed is:

1. A method for providing shielding to a patient during a radiation treatment, the method including:
   locating at least one shield device over at least one portion of the patient to be shielded, the at least one shield device including:
   a plurality of overlapping and interconnected shield elements that form a sheet including at least one substantially configurable edge;
   substantially aligning at least one configurable edge of the at least one shield device with at least one field edge of a treatment zone of the patient to leave the treatment zone exposed including displacing one or more edge shield elements relative to one or more other shield elements to change a shape of the at least one configurable edge; and
   subjecting the patient to a radiation treatment.

2. The method of claim 1 wherein the treatment zone is a breast of the patient, the method including placing the at least one shield device over the contralateral breast of the patient.

3. The method of claim 1 including aligning the at least one configurable edge of the shield device with a non-straight field edge of the treatment zone.

4. The method of claim 1 wherein locating the at least one shield device over at least one portion of the patient to be shielded includes aligning the shield device so that the plurality of shield elements face a direction of incident radiation.

5. The method of claim 1 wherein the plurality of shield elements are arranged in a plurality of rows and wherein the plurality of rows are substantially parallel to at least one edge of the shield device.

6. The method of claim 5 wherein the at least one configurable edge is substantially parallel to the plurality of rows.

7. The method of claim 6 including aligning the at least one configurable edge with a substantially sagittal field edge of the treatment zone.

8. The method of claim 1 wherein the at least one shield device includes at least one sheet of scale maille.

9. The method of claim 1 wherein a plurality of the shield elements include at least one of copper, brass, stainless steel, lead, tin, tungsten, silver and gold.

10. The method of claim 9 wherein a plurality of the shield elements are copper.

11. A device for use in radiation therapy of a patient, the device including a plurality of overlapping and interconnected shield elements that form a sheet including at least one configurable edge, the plurality of overlapping and interconnected shield elements including one or more edge shield elements that are displaceable relative to one or more other shield elements to change a shape of the at least one configurable edge to substantially conform the at least one configurable edge to a field edge of a radiation treatment zone of a patient during a radiotherapy procedure.

12. The device of claim 11 wherein the plurality of shield elements are arranged in a plurality of rows and wherein the plurality of rows are substantially parallel to at least one edge of the shield device.

13. The device of claim 12 wherein the at least one configurable edge is substantially parallel to the plurality of rows.

14. The device of claim 11 including at least one sheet of scale maille.

15. The device of claim 11 wherein a plurality of the shield elements are at least one of copper, brass, stainless steel, lead, tin, tungsten, silver and gold.

16. The device of claim 15 wherein a plurality of the shield elements are copper.

* * * * *